(12) United States Patent
Ohkoba et al.

(10) Patent No.: US 10,617,319 B2
(45) Date of Patent: Apr. 14, 2020

(54) PHOTOACOUSTIC APPARATUS

(71) Applicant: CANON KABUSHIKI KAISHA, Tokyo (JP)

(72) Inventors: Minoru Ohkoba, Utsunomiya (JP); Kenichi Nagae, Yokohama (JP); Kazuhito Oka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 399 days.

(21) Appl. No.: 14/948,126

(22) Filed: Nov. 20, 2015

(65) Prior Publication Data

US 2016/0150991 A1 Jun. 2, 2016

(30) Foreign Application Priority Data

Nov. 28, 2014 (JP) ................................. 2014-242455

(51) Int. Cl.
 *A61B 5/0456* (2006.01)
 *A61B 5/00* (2006.01)
 *A61B 5/026* (2006.01)

(52) U.S. Cl.
 CPC .......... *A61B 5/0456* (2013.01); *A61B 5/0095* (2013.01); *A61B 5/7278* (2013.01); *A61B 5/7289* (2013.01); *A61B 5/748* (2013.01); *A61B 5/026* (2013.01); *A61B 5/743* (2013.01)

(58) Field of Classification Search
 CPC . A61B 2576/00; A61B 5/0073; A61B 5/0095; A61B 5/7475
 See application file for complete search history.

(56) References Cited

U.S. PATENT DOCUMENTS

| 4,549,552 | A | 10/1985 | Groch |
| 4,907,596 | A | 3/1990 | Schmid |
| 2005/0150309 | A1 | 7/2005 | Beard |
| 2007/0015978 | A1* | 1/2007 | Kanayama ........... A61B 5/0095 600/310 |
| 2008/0009705 | A1* | 1/2008 | Furudate ............... A61B 5/055 600/410 |

(Continued)

FOREIGN PATENT DOCUMENTS

| CN | 101861120 A | 10/2010 |
| JP | 2013-248077 A | 12/2013 |

(Continued)

OTHER PUBLICATIONS

Bin Luo, An Improved Monte Carlo Diffusion Hybrid Model for Light Reflectance by Turbid Media, Optics Express, May 14, 2007, pp. 5905-5918 vol. 15 No. 10.

*Primary Examiner* — Mark D Remaly

(74) *Attorney, Agent, or Firm* — Canon U.S.A. Inc., IP Division

(57) ABSTRACT

A photoacoustic apparatus sets a light irradiation timing such that a subject is irradiated with pulsed light at least once within a period extending from a start timing determined on the basis of a generation timing of an R-wave in an electrocardiogram signal to a point at which a first time extending from the generation timing of the R-wave in the electrocardiogram signal to a generation timing of a T-wave in the electrocardiogram signal elapses, and sets the light irradiation timing such that the subject is not irradiated with the pulsed light in a period outside the period extending from the start timing to a point at which the first time elapses.

15 Claims, 3 Drawing Sheets

(56) References Cited

U.S. PATENT DOCUMENTS

| | | | |
|---|---|---|---|
| 2009/0066949 A1* | 3/2009 | Masumura | A61B 5/0073 356/326 |
| 2013/0123604 A1 | 5/2013 | Oyama | |
| 2013/0216114 A1* | 8/2013 | Courtney | A61B 5/0066 382/130 |
| 2013/0324855 A1 | 12/2013 | Lisogurski | |
| 2014/0198606 A1 | 7/2014 | Morscher | |

FOREIGN PATENT DOCUMENTS

| | | |
|---|---|---|
| JP | 2014-100244 A | 6/2014 |
| JP | 2014-128455 A | 7/2014 |
| JP | 2016-042922 A | 4/2016 |
| WO | 2013/181377 A1 | 12/2013 |

* cited by examiner

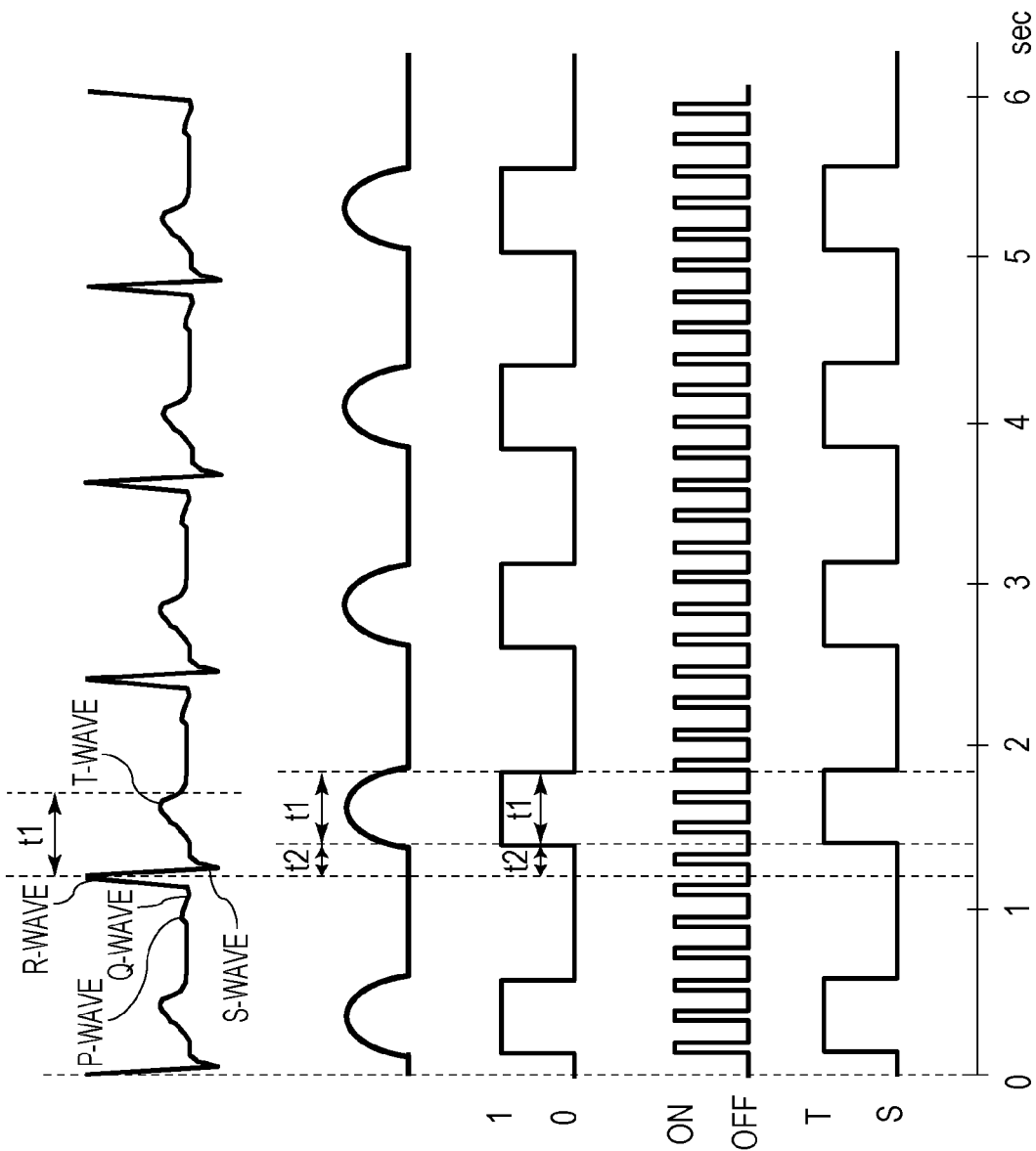

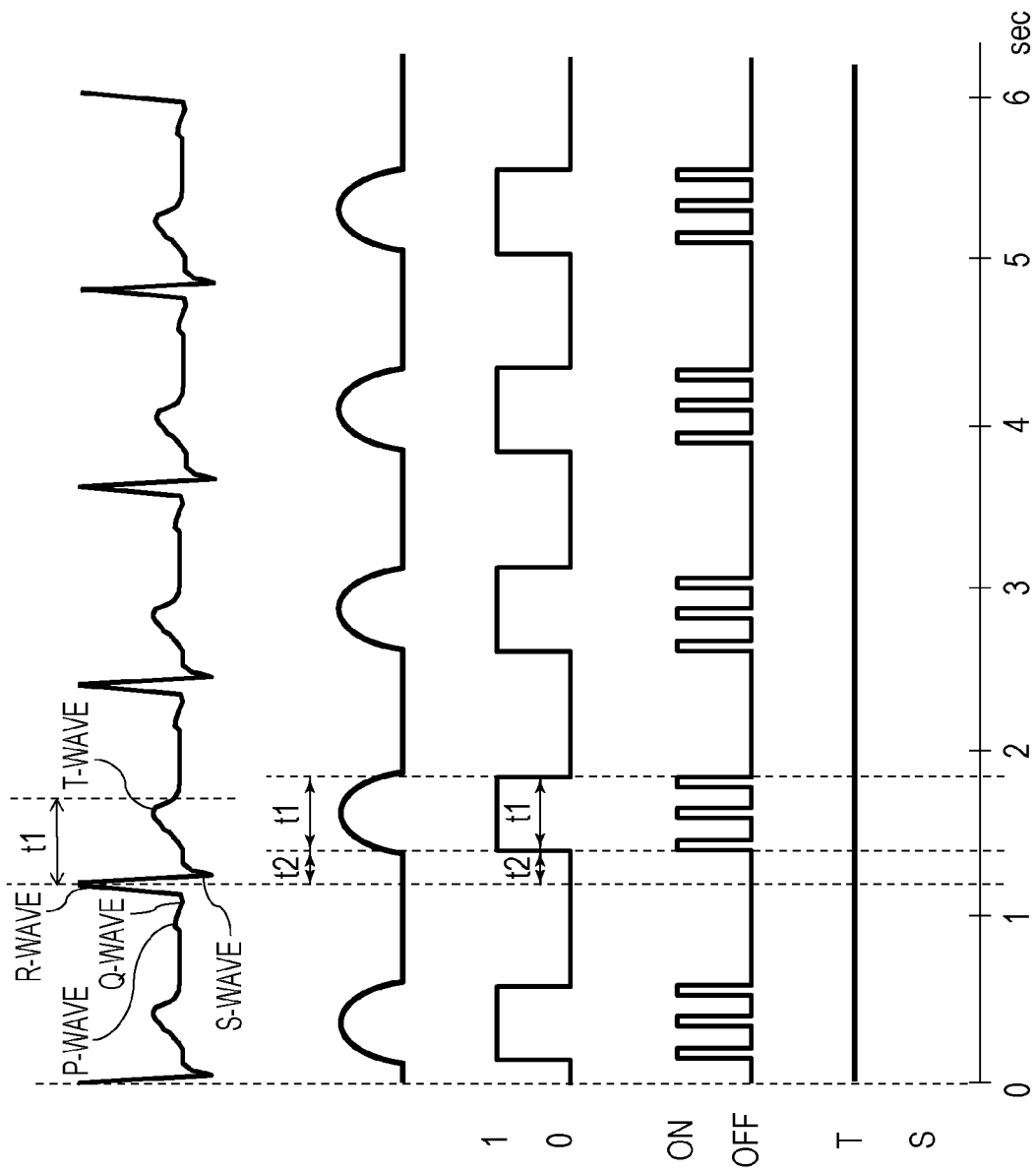

PHOTOACOUSTIC APPARATUS

BACKGROUND OF THE INVENTION

Field of the Invention

The present invention relates to photoacoustic apparatuses that utilizes photoacoustic effects.

Description of the Related Art

Photoacoustic imaging is one of the imaging techniques that utilize light. In photoacoustic imaging, a subject is irradiated with pulsed light generated by a light source. The irradiation light propagates and is scattered inside the subject and is absorbed at a plurality of sites inside the subject, and a photoacoustic wave is generated in turn. The photoacoustic wave is converted to an electric signal by a transducer, and the electric signal is analyzed and processed by a processing device. Thus, information pertaining to values indicative of optical characteristics inside the subject is acquired.

A generated sound pressure (hereinafter, also referred to as an initial sound pressure) $P_0$ of a photoacoustic wave generated from a light absorber inside the subject can be expressed through the following expression.

$$P_0 = \Gamma \cdot \mu_a \cdot \Phi \quad (1)$$

Herein, $\Gamma$ represents the Gruneisen coefficient and is obtained by dividing the product of the coefficient of cubical expansion $\beta$ and the square of the speed of sound c by the specific heat under constant pressure $C_p$. The symbol $\Phi$ represents the quantity of light at a given location (local region) (i.e., the quantity of light that has reached the absorber, which is also referred to as optical fluence).

The initial sound pressure $P_0$ can be obtained by using a reception signal (PA signal) output from a probe that has received a photoacoustic wave.

It is known that the Gruneisen coefficient takes a substantially constant value for each given tissue, and thus it is possible to obtain the product of the optical absorption coefficient $\mu_a$ and the quantity of light $\Phi$, or in other words, the optical energy absorption density by measuring and analyzing the change over time of the PA signals at a plurality of sites.

Japanese Patent Laid-Open No. 2013-248077 discloses a photoacoustic image generation apparatus that generates a photoacoustic image of a blood vessel on the basis of a photoacoustic wave generated from light.

In a case in which hemoglobin serves as a light absorber that is to be measured, the amount of hemoglobin is small in a region in which the blood volume within the blood vessel is small, and thus the optical absorption coefficient in that region is relatively low. Therefore, the sound pressure of the photoacoustic wave that is generated in accordance with the expression (1) tends to be low. In other words, the S/N ratio of a reception signal of a photoacoustic wave generated in a region in which the blood volume is small tends to be relatively low. Accordingly, when subject information of a target region is to be obtained by a photoacoustic apparatus, the accuracy of the acquired subject information may deteriorate in a region in which the blood volume is small.

SUMMARY OF THE INVENTION

An aspect of the present disclosure provides a photoacoustic apparatus that includes a control unit configured to set a light irradiation timing, a light irradiation unit configured to irradiate a subject with pulsed light at the light irradiation timing, a reception unit configured to receive a photoacoustic wave generated as the subject is irradiated with the pulsed light from the light irradiation unit and to output a signal, an electrocardiogram acquisition unit configured to acquire an electrocardiogram signal of the subject, and a subject information acquisition unit configured to acquire subject information on the basis of the signal. The control unit is configured to set the light irradiation timing such that the subject is irradiated with the pulsed light at least once within a period extending from a start timing determined on the basis of a generation timing of an R-wave in the electrocardiogram signal to a point at which a first time extending from the generation timing of the R-wave in the electrocardiogram signal to a generation timing of a T-wave in the electrocardiogram signal elapses, and set the light irradiation timing such that the subject is not irradiated with the pulsed light in a period outside the period extending from the start timing to a point at which the first time elapses.

Further features of the present invention will become apparent from the following description of exemplary embodiments with reference to the attached drawings.

BRIEF DESCRIPTION OF THE DRAWINGS

FIGS. 3A, 3B, 3C, and 3D illustrate various sequences according to the exemplary embodiment.

FIGS. 4A, 4B, 4C, and 4D illustrate another example of the various sequences according to the exemplary embodiment.

DESCRIPTION OF THE EMBODIMENTS

Figure 1:
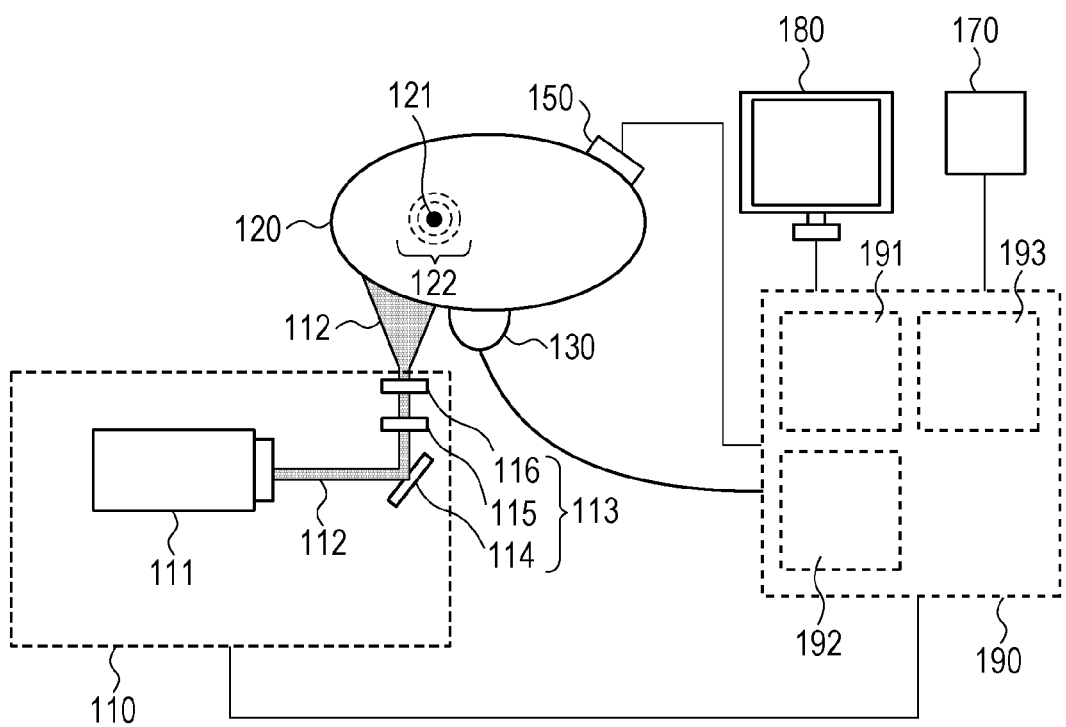
FIG. 1 illustrates a configuration of a photoacoustic apparatus according to an exemplary embodiment.

Hereinafter, an exemplary embodiment of the present invention will be described in detail with reference to the drawings. It is to be noted that identical constituent elements are generally given identical reference characters, and descriptions thereof will be omitted.

First Exemplary Embodiment

A photoacoustic apparatus according to the present exemplary embodiment acquires subject information on the basis of a reception signal of a photoacoustic wave. The subject information according to the present exemplary embodiment is information pertaining to a subject obtained from a reception signal of a photoacoustic wave generated through photoacoustic effects. Specifically, the subject information contains the generated sound pressure (initial sound pressure), the optical energy absorption density, the optical absorption coefficient, the concentration of a substance constituting a tissue, and so on. Examples of the concentration of a substance include the oxygen saturation, the oxyhemoglobin concentration, the deoxyhemoglobin concentration, and the total hemoglobin concentration. The total hemoglobin concentration is the sum of the oxyhemoglobin concentration and the deoxyhemoglobin concentration. In addition, distribution data, such as the optical absorption coefficient distribution and the oxygen saturation distribution, may also serve as the subject information.

Basic Configuration

The basic configuration of the photoacoustic apparatus according to the present exemplary embodiment will be described with reference to FIG. 1.

FIG. 1 schematically illustrates the configuration of the photoacoustic apparatus according to the present exemplary embodiment. The photoacoustic apparatus according to the present exemplary embodiment includes a light irradiation unit 110, an acoustic wave reception unit 130, an electrocardiogram acquisition unit 150, an input unit 170, a display unit 180, and a processing unit 190. The light irradiation unit 110 includes a light source 111 and an optical system 113. The configuration of the light source 110 and the optical system 113 will be described later in detail.

The light source 111 emits pulsed light 112, and the pulsed light 112 is guided by the optical system 113. The pulsed light 112 emitted from the optical system 113 is incident on a subject 120 and then reaches a light absorber 121 inside the subject 120. The light absorber 121 can typically be a blood vessel or in particular a substance such as hemoglobin present in the blood vessel inside an organism, a tumor, or the like. The light absorber 121 absorbs the energy of the light and generates a photoacoustic wave 122. The generated photoacoustic wave 122 propagates inside the subject 120 and reaches the acoustic wave reception unit 130.

The acoustic wave reception unit 130 receives the photoacoustic wave 122 and outputs a time-series reception signal in turn. The processing unit 190 successively receives a reception signal output from the acoustic wave reception unit 130.

The processing unit 190 generates subject information in a target region on the basis of the input time-series reception signal. The processing unit 190 then transmits data of the generated subject information to the display unit 180 and displays, on the display unit 180, an image, a numerical value, and so on of the subject information in the target region. The target region may be set in advance or may be input by a user through the input unit 170. The target region is set so as to include at least a portion of the subject 120. The method for acquiring the subject information will be described later in detail.

In a case in which hemoglobin is to serve as a light absorber, the amount of hemoglobin is small in a region in which the blood volume within the blood vessel is small, and thus the optical absorption coefficient in that region is relatively low. Therefore, the sound pressure of the photoacoustic wave that is generated in accordance with the expression (1) tends to be low. In other words, the S/N ratio of a reception signal of a photoacoustic wave generated in a region in which the blood volume is small is relatively low. In addition, in a case in which the blood volume is extremely small, the reception signal of a photoacoustic wave may be drowned out by noise. Accordingly, when subject information in a target region is to be obtained by a photoacoustic apparatus, the accuracy of the acquired subject information may deteriorate in a region in which the blood volume is small.

In view of such an issue, the photoacoustic apparatus according to the present exemplary embodiment includes the electrocardiogram acquisition unit 150 configured to acquire an electrocardiogram signal of the subject 120. The condition of the heart of the subject 120 can be estimated from the waveform of an electrocardiogram signal acquired by the electrocardiogram acquisition unit 150, and the blood flow condition of the subject 120 can thus be estimated. Thus, the processing unit 190 sets the light irradiation timing of the light irradiation unit 110 such that the light irradiation unit 110 does not irradiate the subject 120 with the pulsed light 112 while the blood volume in the target region is small, on the basis of the electrocardiogram signal of the subject 120 acquired by the electrocardiogram acquisition unit 150. In addition, the processing unit 190 sets the light irradiation timing of the light irradiation unit 110 such that the light irradiation unit 110 irradiates the subject 120 with the pulsed light 112 while the blood volume in the target region is large.

Setting the light irradiation timing in this manner makes it possible to selectively irradiate the subject 120 with the pulsed light 112 while the blood volume is large, or in other words, while the amount of hemoglobin serving as the light absorber is large. Thus, a number of reception signals of photoacoustic waves having a high S/N ratio can be acquired. In addition, according to the present exemplary embodiment, it is unlikely that a reception signal of a photoacoustic wave having a low S/N ratio generated while the blood volume is small is included, and thus the subject information in the target region can be acquired with high accuracy. The light irradiation timing will be described later in detail.

Hereinafter, each of the constituting blocks of the photoacoustic apparatus according to the present exemplary embodiment will be described.

Light Source 111

The light source 111 may be a pulsed light source that can generate nanosecond to microsecond pulsed light. Specifically, the pulse duration is preferably in a range approximately from 1 to 100 nanoseconds. In addition, the wavelength is preferably in a range approximately from 400 nm to 1600 nm. In particular, light at a wavelength in a visible light range (400 nm or longer and 700 nm or shorter) may be used when a blood vessel near the surface of an organism is to be imaged at high resolution. In the meantime, light at a wavelength at which the light is not absorbed in large quantity by a background tissue of an organism (700 nm or longer and 1100 or shorter) may be used when a site deep inside the organism is to be imaged. Alternatively, radiation in a terahertz wave range, a microwave range, or a radio wave range can also be used.

The light source 111 may preferably be a laser. In addition, in a case in which a measurement is to be carried out by using light with different wavelengths, a laser whose oscillation wavelength can be varied may be used. In a case in which the subject 120 is to be irradiated with light with different wavelengths, a plurality of lasers that emit light at mutually different wavelengths may be used while switching the oscillation or while irradiating the subject 120 in an alternating manner. Even when a plurality of lasers are used, the lasers are collectively referred to as a light source.

A variety of lasers including a solid-state laser, a gas laser, a dye laser, and a semiconductor laser can be used as the aforementioned laser. In particular, a pulse laser, such as an Nd:YAG laser and an alexandrite laser, may be suitably used. In addition, a Ti:Sapphire laser or an optical parametric oscillator (OPC) laser that is pumped by an Nd:YAG laser may also be used. Alternatively, a light-emitting diode can be used instead of a laser.

Optical System 113

The optical system 113 can deliver the pulsed light 112 from the light source 111 to the subject 120. Optical elements including a lens, a mirror, and an optical fiber can be used as the optical system 113. In addition, the optical system 113 according to the present exemplary embodiment includes an optical mirror 114 for changing the traveling direction of the pulsed light 112, a light controlling unit 115, and a diffusing plate 116.

In a biological information acquisition device in which a subject, such as a breast, is examined, pulsed light may have its beam diameter expanded by the diffusing plate 116 or the like at the light emission portion of the optical system 113, and the subject may be irradiated with such pulsed light. On the other hand, in a photoacoustic microscope, a lens or the like may be provided at the light emission portion of the optical system 113 in order to increase the resolution, and the subject is irradiated with a focused beam.

In addition, the optical system 113 can include the light controlling unit 115 that can vary the attenuation of the pulsed light 112 emitted by the light source 111. The light controlling unit 115 can be constituted by any device that can vary the attenuation of the pulsed light 112, such as a mechanical shutter and a liquid-crystal shutter. It is to be noted that, in the present specification, the expression "not irradiating a subject with pulsed light" encompasses a case in which the intensity of the irradiating pulsed light is set to 0 as well as a case in which the subject is irradiated with pulsed light whose intensity has been attenuated to a level at which it is difficult to detect a photoacoustic wave generated from the pulsed light. In the present disclosure, it can be said that the optical system for regulating the attenuation of the pulsed light 112 weights the attenuation of the pulsed light 112 in accordance with the blood volume estimated from an electrocardiogram signal.

In addition, the optical system 113 may be configured to be movable relative to the subject 120, and the subject 120 can then be imaged in a broad range.

It is also possible to directly irradiate the subject 120 with light from the light source 111 without involving the optical system 113.

Subject 120

Although the subject 120 does not constitute part of the photoacoustic apparatus according to the present disclosure, the subject 120 will be described hereinafter. The photoacoustic apparatus according to the present exemplary embodiment is primarily used for making a diagnosis of a malignant tumor or a vascular disease in human and animals or for a follow-up observation of chemotherapy. Thus, the subject 120 can be an organism, or specifically can be such sites as a breast, a cervix, an abdomen of a human body or an animal on which a diagnosis is to be made.

In addition, the light absorber 121 present inside the subject 120 may have a high optical absorption coefficient relative to other portions inside the subject 120. For example, in a case in which a human body is a measurement target, the light absorber 121 can be oxyhemoglobin, deoxyhemoglobin, a blood vessel in which oxyhemoglobin and deoxyhemoglobin are present in a large amount, or a neovessel formed in the vicinity of a tumor.

Acoustic Wave Reception Unit 130

The acoustic wave reception unit 130 includes one or more conversion elements and a housing. For the conversion elements, any conversion element that can receive an acoustic wave and convert the acoustic wave to an electric signal can be used, and examples of such include a piezoelectric element that utilizes a piezoelectric phenomenon, such as lead zirconate titanate (PZT); a conversion element that utilizes resonance of light; and an electrostatic capacitance type conversion element, such as a capacitive micromachined ultrasonic transducer (CMUT). In a case in which a plurality of conversion elements are provided, the conversion elements may be arrayed along a plane or a curved surface referred to as a 1D array, a 1.5D array, a 1.75D array, or a 2D array.

In addition, in order to acquire the subject information in a broad range, the acoustic wave reception unit 130 may be configured to be moved relative to the subject 120 mechanically by a scanning mechanism (not illustrated). The optical system 113 (irradiation position of the pulsed light 112) and the acoustic wave reception unit 130 may be moved in synchronization.

In a case in which the acoustic wave reception unit 130 of a hand-held type is to be used, the acoustic wave reception unit 130 includes a grip portion that allows the user to hold the acoustic wave reception unit 130. The acoustic wave reception unit 130 may include an acoustic lens provided on a reception surface thereof. In addition, the acoustic wave reception unit 130 may include a plurality of conversion elements.

The acoustic wave reception unit 130 may also include an amplifier configured to amplify a time-series analog signal output from a conversion element.

Electrocardiogram Acquisition Unit 150

The electrocardiogram acquisition unit 150 acquires an electrocardiogram signal of the subject 120. Typically, the electrocardiogram acquisition unit 150 includes an induction electrode for extracting an electrocardiogram signal, an amplifier, and an A/D converter. For example, the electrocardiogram acquisition unit 150 can be constituted by a device disclosed in Japanese Patent Laid-Open No. 2014-128455 or in Japanese Patent Laid-Open No. 2014-100244. On the basis of the electrocardiogram signal acquired by the electrocardiogram acquisition unit 150, the condition of the heart of the subject 120 can be estimated. In addition, the blood flow through the blood vessel can also be estimated on the basis of the condition of the heart estimated from the electrocardiogram signal.

Input Unit 170

The input unit 170 accepts a variety of inputs from a user (primarily a tester, such as a person in the medical profession) and transmits the input information to a component such as the processing unit 190 through a system bus. For example, the input unit 170 allows the user to set parameters related to imaging, to issue an instruction for starting the imaging, to set observation parameters including the range and the shape of the target region, and to carry out an image processing operation on an image.

The input unit 170 is constituted by a mouse, a keyboard, a touch panel, or the like, and issues an event notification to software such as the operating system (OS) operating on a control unit 193 in accordance with an operation of the user. Meanwhile, a hand-held type photoacoustic apparatus may be provided with an input unit 170 for providing an instruction for driving the light irradiation unit 110. Such an input unit 170 can be constituted by a button-type switch provided on a probe, a foot switch, or the like.

Display Unit 180

The display unit 180 can be constituted by a display, such as a liquid-crystal display (LCD), a cathode-ray tube (CRT), and an organic electroluminescence (EL) display. The display unit 180 may not be included in the photoacoustic apparatus according to the present exemplary embodiment, and the display unit 180 may be prepared separately and connected to the photoacoustic apparatus.

Processing Unit 190

The processing unit 190 serving as a computer includes an arithmetic operation unit 191, a storage unit 192, and the control unit 193.

The arithmetic operation unit 191 collects a time-series analog reception signal output from the acoustic wave reception unit 130 and carries out signal processing including amplification of the reception signal, A/D conversion of the analog reception signal, storage of the digitized reception signal. The arithmetic operation unit 191 that carries out such processing can be constituted by a circuit typically referred to as a data acquisition system (DAS). Specifically, the arithmetic operation unit 191 is constituted by an amplifier that amplifies a reception signal, an A/D converter that digitizes an analog reception signal, and the like.

In addition, the arithmetic operation unit 191 can acquire information on the generated sound pressure at each location inside the subject. The information on the generated sound pressure at each location inside the subject is also referred to as an initial sound pressure distribution inside the subject. In a case in which the photoacoustic apparatus is a photoacoustic tomography apparatus, the arithmetic operation unit 191 reconstructs an image by using an acquired reception signal and can thus obtain data of the generated sound pressure corresponding to a position on the two-dimensional or three-dimensional spatial coordinates. The arithmetic operation unit 191 can employ a publicly known reconstruction technique, such as the universal back projection (UBP), the filtered back projection (FBP), and a model-based technique, as a technique for reconstructing an image. In addition, the arithmetic operation unit 191 may employ delay and sum processing as a technique for reconstructing an image.

The arithmetic operation unit 191 may detect an envelope of an acquired reception signal and then plot an amplitude value in the time-axis direction of the signal whose envelope has been detected in the directionality direction of the conversion element (typically in the depthwise direction). The arithmetic operation unit 191 carries out such processing at each of the positions of the conversion elements and can thus acquire the initial sound pressure distribution data. In particular, in a case in which photoacoustic apparatus is a photoacoustic microscope, the above-described technique may be employed.

The arithmetic operation unit 191 that carries out processing of acquiring the information on the generated sound pressure can be constituted by a processor, such as a central processing unit (CPU) and a graphics processing unit (GPU), or an arithmetic operation circuit, such as a field programmable gate array (FPGA) chip. It is to be noted that the arithmetic operation unit 191 may be constituted not only by a single processor or arithmetic operation circuit but also by a plurality of processors or arithmetic operation circuits.

The storage unit 192 can store the reception signal that has been subjected to A/D conversion, various pieces of distribution data, display image data, various measurement parameters, and so on. In addition, the storage unit 192 can store the processes that are carried out in the method for acquiring subject information, which will be described later, in the form of a program that is to be executed by the control unit 193 in the processing unit 190. The storage unit 192 that stores the program is a non-transitory recording medium. The storage unit 192 is typically constituted by a storage medium, such as a first-in first out (FIFO) memory, a read-only memory (ROM), a random-access memory (RAM), or a hard disk. The storage unit 192 may be constituted not only by a single storage medium but also by a plurality of storage media.

In addition, the processing unit 190 includes the control unit 193 for controlling the operation of each of the constituting blocks of the photoacoustic apparatus. The control unit 193 supplies necessary control signals and data to each of the constituting blocks of the photoacoustic apparatus through a bus. Specifically, the control unit 193 supplies a light emission control signal for instructing the light source 111 to emit light, a reception control signal for a conversion element inside the acoustic wave reception unit 130, and so on. The control unit 193 is typically constituted by a CPU.

It is to be noted that the components included in the processing unit 190 may be integrated into a single piece of device or may be implemented as respectively separate components. In addition, the arithmetic operation unit 191 and the control unit 193 may be implemented by a single piece of device. In other words, the processing unit 190 may include a single device that carries out the functions of the arithmetic operation unit 191 and of the control unit 193.

Method for Acquiring Subject Information

Figure 2:
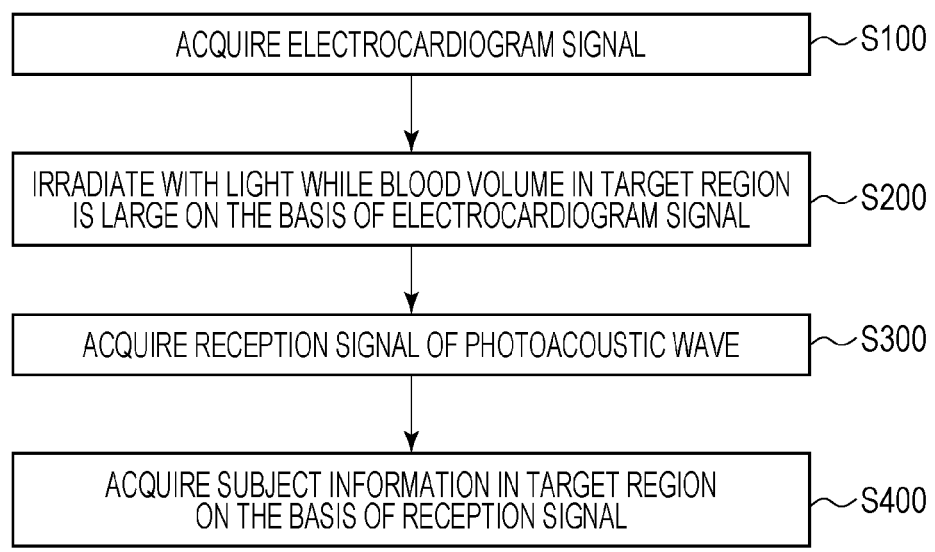
FIG. 2 is a flowchart of a method for acquiring subject information according to the exemplary embodiment.

Subsequently, the process through which the photoacoustic apparatus according to the present exemplary embodiment acquires the subject information will be described with reference to FIG. 2. The control unit 193 reads out the program that is stored in the storage unit 192 and that describes the method for acquiring the subject information, and causes the photoacoustic apparatus to execute the following method for acquiring the subject information.

S100: Step of Acquiring Electrocardiogram Signal

In this step, the electrocardiogram acquisition unit 150 acquires an electrocardiogram signal of the subject 120 and transmits the acquired electrocardiogram signal to the processing unit 190. The electrode provided in the electrocardiogram acquisition unit 150 is disposed as appropriate so that an electromyogram signal (electrocardiogram signal) pertaining to the heart can be acquired.

FIG. 3A illustrates the waveform of a typical electrocardiogram signal acquired by the electrocardiogram acquisition unit 150. The electrocardiogram signal illustrated in FIG. 3A has a waveform with a cycle of approximately 1.2 second. Typically, the waveform of an electrocardiogram signal has a shape that is a composite of a P-wave, a Q-wave, an R-wave, an S-wave, and a T-wave. Typically, a period extending from the apex of the R-wave to a point close to the end of the T-wave corresponds to the ventricular systole, and the blood is ejected into the artery. In addition, the period extending from a point close to the end of the T-wave to the apex of the R-wave corresponds to the ventricular diastole. In the present specification, a time t1 extending from the apex of the R-wave to a point close to the end of the T-wave is referred to as a first time extending from the generation timing of the R-wave to the generation timing of the T-wave.

FIG. 3B is a graph illustrating a change in the blood volume in the target region. As described above, with respect to the condition of the heart, the ventricular systole starts at the R-wave in the electrocardiogram signal, and the ejection of the blood into the artery starts. However, as can be seen from FIG. 3B, the blood volume in the target region does not start to increase at the generation timing of the R-wave but starts to increase with a time lag of a time t2 extending from the generation timing of the R-wave to a point at which the blood corresponding to the ventricular contraction reaches the target region. Then, it is considered that a period in which the blood volume is increased is retained for the time t1 of the ventricular systole after the time t2 has elapsed since the generation timing of the R-wave.

In the present specification, the time t2 extending from the generation timing of the R-wave to the point at which the blood flow corresponding to the ventricular contraction reaches the target region is also referred to as a delay time.

S200: Step of Irradiating Subject with Light while Blood Volume in Target Region is Large on the Basis of Electrocardiogram Signal In this step, the control unit 193 determines the timing at which the blood volume in the target region is large on the basis of the electrocardiogram signal acquired by the electrocardiogram acquisition unit 150. Then, the control unit 193 sets the light irradiation timing of the light irradiation unit 110 such that the light irradiation unit 110 irradiates the subject 120 with the pulsed light 112 at the determined timing.

Meanwhile, the control unit 193 sets the light irradiation timing of the light irradiation unit 110 such that the light irradiation unit 110 does not irradiate the subject 120 with the pulsed light 112 while the blood volume in the target region is small.

The control unit 193 supplies an irradiation control signal to the light irradiation unit 110 on the basis of the electrocardiogram signal acquired in S100. The light irradiation unit 110 irradiates the subject 120 with the pulsed light 112 at the light irradiation timing that is based on the irradiation control signal supplied from the control unit 193. The pulsed light 112 is absorbed by the subject 120, and the photoacoustic wave 122 is generated through a photoacoustic effect.

FIG. 3C illustrates an example of the irradiation control signal that the control unit 193 supplies to the light irradiation unit 110. FIG. 3C indicates that the light irradiation unit 110 irradiates the subject 120 when the signal is 1 and does not irradiate the subject 120 when the signal is 0. The control unit 193 supplies the irradiation control signal such that the light irradiation unit 110 irradiates the subject 120 with the pulsed light 112 during a period in which the time t1 elapses after the delay time t2 has passed since the generation timing of the R-wave. In other words, the control unit 193 supplies the irradiation control signal such that the light irradiation unit 110 irradiates the subject 120 while the blood flow produced by the ventricular contraction is present and the blood volume is large. Meanwhile, the control unit 193 supplies the irradiation control signal such that the light irradiation unit 110 does not irradiate the subject 120 in a period outside the period in which the blood volume is large.

The speed of light is tremendously higher than the speed of the photoacoustic wave, and thus it is possible to presume that photoacoustic waves are generated simultaneously at respective positions within the target region at the timing at which the subject 120 is irradiated with the pulsed light 112. In the present specification, the timing at which the subject 120 is irradiated with the pulsed light 112 is regarded as the timing at which the photoacoustic wave produced by that pulsed light 112 is generated.

In addition, typically, the time t1 extending from the generation timing of the R-wave to the generation timing of the T-wave is known to fall within a range from 0.3 second to 0.45 second inclusive. Thus, the light irradiation unit 110 may irradiate the subject 120 for a predetermined period of time ranging from 0.3 second to 0.45 second inclusive, which corresponds to the period in which the blood volume is large, after the time t2 has elapsed since the generation timing of the R-wave.

Here, the control unit 193 detects the generation timing of a specific wave, such as the R-wave or the T-wave, from the electrocardiogram signal. For example, the control unit 193 can detect, as the R-wave, the wave in the electrocardiogram signal that has an amplitude greater than a predetermined amplitude. In addition, for example, the control unit 193 can subject the electrocardiogram signal to template matching in which the electrocardiogram signal is compared against the template waveform of the R-wave or the T-wave stored in the storage unit 192, and detect a wave showing high similarity as the R-wave or the T-wave. Any method that can detect a characteristic waveform of the R-wave, T-wave, and so on may be employed as the method for detecting a specific wave.

The blood flow corresponding to the ventricular contraction reaches the target region after the time indicated by a value obtained by dividing the length of the blood vessel between the heart and the target region by the blood flow velocity passes since the R-wave has been generated. Therefore, the control unit 193 can determine the start timing of the light irradiation on the basis of the generation timing of the R-wave, information on the length of the blood vessel between the heart and the target region, and information on the blood flow velocity. However, in order to determine the start timing of the light irradiation as described above, the distance between the heart and the target region and the blood flow velocity need to be measured for each subject, and thus the scale of the apparatus may increase.

Therefore, the light irradiation timing may be selected from a set of timings determined in advance for each site in the target region. In other words, the storage unit 192 may include a relation table defining the relation between the type of site in the target region and the delay time t2. In addition, the photoacoustic apparatus may include an input unit 170 configured to allow the user to input the type of site in the target region. For example, the input unit 170 can be configured to allow the user to select a type of site in the target region from a plurality of types of sites displayed on the display unit 180. The control unit 193 can then read out the delay time t2 corresponding to the type of site input through the input unit 170 from the relation table stored in the storage unit 192. The control unit 193 can detect the generation timing of the R-wave from the electrocardiogram signal and can start the light irradiation when the delay time t2 that has been read out from the storage unit 192 has elapsed since the detected timing.

Although the type of site in the target region is described herein as the information necessary for determining the delay time t2, the information necessary for determining the delay time t2 is not limited thereto. For example, the delay time t2 is considered to vary with age or the like of the subject even when the type of site in the target region is the same. Therefore, the input unit 170 may be configured to be capable of accepting an input of such information as the age of the subject in addition to the type of site. In other words, the input unit 170 may be configured to be capable of accepting an input of at least the type of site in the target region. Then, the control unit 193 may read out, from the relation table, the delay time t2 corresponding to the input information such as the age of the subject.

In addition, in a case in which a target site of the photoacoustic apparatus is determined in advance, the storage unit 192 may store information on the delay time t2 obtained in advance. The control unit 193 can then detect the generation timing of the R-wave from the electrocardiogram signal and can start the light irradiation when the delay time t2 stored in the storage unit 192 has elapsed since the detected timing.

In a case in which the period extending from the generation timing of the R-wave to a point at which the blood flow corresponding to the ventricular contraction reaches the target region can be ignored, the generation timing of the R-wave may serve as the start timing of the light irradiation. In other words, the delay time t2 may be set to 0 in this case.

In addition, the light irradiation unit 110 may irradiate the subject 120 with a single pulse of light during a period in which the blood volume is large or may irradiate the subject 120 with multiple pulses of light. In other words, the light irradiation unit 110 may irradiate the subject 120 at least once with the pulsed light 112 during the period in which the blood volume is large.

In a case in which the light source 111 is constituted by a solid-state laser or the like pumped by a lamp that easily produces heat, the light source 111 may be caused to emit light at a constant repetition rate so that the light source 111 can be driven stably. The timing at which the subject 120 is irradiated with light may be controlled by controlling the optical system 113. FIG. 3D illustrates the drive sequence of the light source 111 and indicates that the light source 111 emits light in an on-state and does not emit light in an off-state. As can be seen from FIG. 3D, the light source 111 emits light at a constant repetition rate (5 Hz) as described above. In addition, FIG. 3E illustrates the drive sequence of the optical system 113 and indicates that the light controlling unit 115 transmits the light from the light source 111 during the T-period and the light controlling unit 115 blocks the light from the light source 111 during the S-period. In this manner, the light irradiation unit 110 can selectively irradiate the subject 120 with the pulsed light 112 in accordance with the irradiation control signal illustrated in FIG. 3C.

However, the method for controlling the light irradiation timing of the light irradiation unit 110 is not limited to the method illustrated in FIGS. 3A to 3E, and any method that allows the subject 120 to be selectively irradiated with light while the blood volume is large can be employed. For example, as illustrated in FIGS. 4A to 4E, the light irradiation timing may be controlled by the control unit 193 controlling the light emission timing of the light source 111. The types of the sequences illustrated in FIGS. 4A to 4E are identical to those illustrated in FIGS. 3A to 3E. As can be seen from FIG. 4D, the light source 111 is controlled by the control unit 193 such that the light source 111 does not emit light while the blood volume is small and emits light while the blood volume is large. Meanwhile, the light controlling unit 115 is controlled by the control unit 193 such that the light controlling unit 115 constantly transmits the pulsed light 112 generated by the light source 111. In this case, the light irradiation unit 110 does not have to include the light controlling unit 115. In addition, in this case, the frequency at which the light source 111 emits light can be reduced, and thus the wear of the components constituting the light source 111 can be reduced.

Meanwhile, a case in which an input unit 170 serving as a switch for accepting an instruction for driving the light irradiation unit 110 from the user, as in the hand-held type photoacoustic apparatus, is provided will now be considered. In this case, the light irradiation unit 110 may be configured to irradiate the subject 120 with the pulsed light 112 while the blood volume is large on the basis of the electrocardiogram signal and only upon receiving, through the switch, information pertaining to the instruction for driving the light irradiation unit 110. In other words, the light irradiation unit 110 may not irradiate the subject 120 with the light while the blood volume is small or when the information pertaining to the instruction for driving is not received through the switch.

Although the light irradiation timing is set under the assumption that the blood volume increases during the time t1 corresponding to the ventricular systole that starts when the delay time t2 has elapsed since the generation timing of the R-wave in the present exemplary embodiment, the setting of the light irradiation timing is not limited to such a mode. For example, although the time t1 corresponds to the duration of the ventricular systole, a case can be considered in which the ejection of the blood is mostly completed before the time t1 elapses depending on the accumulated blood volume. In other words, a case can be considered in which the duration of the ventricular systole and the time it takes to eject the blood do not match. In this case, the blood volume may increase only for a duration that is shorter than the time t1. In this case, the control unit 193 may control the light irradiation unit 110 such that the subject 120 is irradiated at least once with the pulsed light 112 while a time t3 elapses after the delay time t2 has elapsed since the generation timing of the R-wave. In other words, the control unit 193 may control the light irradiation unit 110 such that the subject 120 is irradiated with more pulses of the pulsed light 112 while a time that is one-half the voltage application time t1 elapses after the delay time t2 has elapsed since the generation timing of the R-wave than in a period after the aforementioned time has elapsed.

S300: Step of Acquiring Reception Signal of Photoacoustic Wave

In this step, the acoustic wave reception unit 130 receives the photoacoustic wave 122 generated as the subject 120 is irradiated with the pulsed light 112 in S200, and outputs a time-series analog reception signal. The arithmetic operation unit 191 collects the time-series analog reception signal output from the acoustic wave reception unit 130 and carries out amplification processing of the reception signal and A/D conversion processing of the analog reception signal. The arithmetic operation unit 191 then stores the digitized reception signal into the storage unit 192. The time-series reception signal data stored in the storage unit 192 is also referred to as photoacoustic data. In the present disclosure, a reception signal is a concept that encompasses an analog signal as well as a digital signal. In this step, a signal with a high S/N ratio that is obtained as the subject 120 is irradiated with the pulsed light 112 while the blood flow volume in the target region is large can selectively be acquired.

S400: Step of Acquiring Subject Information in Target Region on the Basis of Reception Signal In this step, the arithmetic operation unit 191 serving as the subject information acquisition unit acquires the subject information in the target region on the basis of the reception signal acquired in S300. In the present exemplary embodiment, the arithmetic operation unit 191 computes, as the subject information, the generated sound pressure information of the photoacoustic wave at each location within the target region, or in other words, computes the initial sound pressure distribution on the basis of the reception signal stored in the storage unit 192 and stores the computed subject information into the storage unit 192.

The initial sound pressure distribution obtained in this step is computed on the basis of the reception signal with a high S/N ratio that has been obtained in S300, and thus the accuracy of the initial sound pressure distribution is high. Therefore, as the arithmetic operation unit 191 displays, on the display unit 180, an image of the initial sound pressure distribution stored in the storage unit 192, a high-quality image having high resolution, high contrast, and so on can be provided to the user.

The arithmetic operation unit 191 may compute the optical fluence of the pulsed light 112 that has reached each location within the target region, or in other words, may compute the light quantity distribution. In the present exemplary embodiment, the arithmetic operation unit 191 can acquire information on the light quantity distribution of the pulsed light 112 within the target region by solving the light diffusion equation described in Bin Luo and Sailing He, Optics Express Vol. 15, Issue 10, pp. 5905-5918 (2007), and can store the acquired information into the storage unit 192.

As long as the light quantity distribution within the target region can be acquired, the arithmetic operation unit 191 may acquire the light quantity distribution through any method.

Subsequently, the arithmetic operation unit 191 may acquire, as the subject information, the optical absorption coefficient distribution within the target region through the expression (1) on the basis of the initial sound pressure distribution and the light quantity distribution within the target region stored in the storage unit 192.

In this step, the arithmetic operation unit 191 may acquire the subject information of a single frame from a time-series reception signal acquired through light irradiation of a single pulse, or may acquire the subject information of a single frame from a plurality of time-series reception signals acquired through multiple instances of light irradiation.

In addition, for example, there may be a case in which the S/N ratio of the acquired reception signal is not sufficiently high at a timing at which the increase in the blood volume is not sufficient even when the delay time t2 has elapsed since the generation timing of the R-wave. Therefore, the arithmetic operation unit 191 may acquire the subject information on the basis of a reception signal having an amplitude greater than a predetermined value.

Through the method for acquiring the subject information described above, an influence of the blood volume in the blood vessel on the subject information to be acquired can be suppressed.

The photoacoustic apparatus according to the present exemplary embodiment can also acquire the optical absorption coefficient distribution in a similar manner by carrying out each of the steps described above with the use of light having different wavelengths. Then, the arithmetic operation unit 191 can also acquire, as the subject information, information on the concentration distribution of a substance constituting the subject 120 on the basis of a plurality of optical absorption coefficient distributions corresponding to the light having mutually different wavelengths.

However, in a case in which light rays at respective wavelengths are to be generated with the use of a single light source, it may take some time to switch the wavelength. If the wavelength is switched while the blood volume is large, the frequency at which the subject can be irradiated with the light while the blood volume is large may decrease, and the accuracy of the subject information may thus be reduced. Therefore, the wavelength may be switched while the blood volume is small. For example, when a cycle is defined as an interval from a given R-wave to a subsequent R-wave, the light irradiation unit 110 irradiates the subject 120 with light at a first wavelength λ1 during a given cycle of an electrocardiogram signal. Then, in a period within that cycle in which the blood volume is small, a wavelength varying mechanism within the light source 111 is driven so as to bring the light source 111 into a state in which the light source 111 can emit light at a second wavelength λ2. Then, within a subsequent cycle, the light irradiation unit 110 irradiates the subject 120 with the light at the second wavelength λ2.

In this manner, the wavelength may be switched within a period in which the blood volume is small and the subject is set not to be irradiated with the light. With this configuration, the subject can be efficiently irradiated with light at a plurality of wavelengths while the blood volume is large without reducing the number of instances of the light irradiation within a period in which the blood volume is large and the subject is set to be irradiated with the light.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-242455 filed Nov. 28, 2014, which is hereby incorporated by reference herein in its entirety.

What is claimed is:

1. A photoacoustic apparatus, comprising:
a control unit configured to set a light irradiation timing;
a light irradiation unit configured to irradiate a subject with pulse light at the light irradiation timing;
a reception unit configured to receive a photoacoustic wave generated in response to an irradiation of the subject by the pulsed light from the light irradiation unit and to output a signal;
an electrocardiogram acquisition unit configured to acquire an electrocardiogram signal of the subject; and
a subject information acquisition unit configured to acquire subject information on the basis of the signal,
an input unit configured to receive an input of a type of site in a target region; and
a storage unit configured to store a relation table containing relationships between the type of the site in the target region and a second time extending from a generation timing of an R-wave in the electrocardiogram signal to an arrival timing at which a blood flow corresponding to the R-wave reaches the target region;
wherein the control unit is configured to read, out of the relation table, the second time that corresponds to the type of the site in the target region input by the input unit, set the light irradiation timing such that the subject is irradiated with the pulsed light at least once during a first time after the second time read out from the relation table has elapsed since the generation timing of the R-wave, wherein the first time is extending from the generation timing of the R-wave in the electrocardiogram signal to a generation timing of a T-wave in the electrocardiogram signal, set the light irradiation timing such that the subject is not irradiated with the pulsed light in a period outside a period extending from a point at which the second time elapses since the generation timing of the R-wave to a point at which the first time elapses.

2. The photoacoustic apparatus according to claim 1, wherein the control unit determines the generation timing of the R-wave and the generation timing of the T-wave in the electrocardiogram signal on the basis of the electrocardiogram signal.

3. The photoacoustic apparatus according to claim 1, wherein the first time is 0.3 second or more to 0.45 second or less.

4. The photoacoustic apparatus according to claim 1, wherein the control unit sets the second timing on the basis of the generation timing of the R-wave in the electrocardiogram signal, information on a distance between a heart of the subject and the target region, and information on a blood flow velocity.

5. The photoacoustic apparatus according to claim 1,
wherein the light irradiation unit includes a light source configured to emit the pulsed light, and
wherein the control unit sets the light irradiation timing by setting a light emission timing of the light source on the basis of the electrocardiogram signal.

6. The photoacoustic apparatus according to claim 1, wherein the light irradiation unit includes
an optical system configured to control an attenuation of the pulsed light from a light source, and
wherein the control unit sets the light irradiation timing by controlling the attenuation of the pulsed light in the optical system on the basis of the electrocardiogram signal.

7. The photoacoustic apparatus according to claim 6,
wherein the optical system is a shutter configured to block the pulsed light from the light source, and
wherein the control unit sets the light irradiation timing by setting whether to cause the shutter to block the pulsed light from the light source on the basis of the electrocardiogram signal.

8. The photoacoustic apparatus according to claim 6, wherein the light irradiation unit includes a light source configured to emit the pulse light at a predetermined repetition rate.

9. The photoacoustic apparatus according to claim 7, wherein the light irradiation unit includes a light source configured to emit the pulsed light at a predetermined repetition rate.

10. The photoacoustic apparatus according to claim 1,
wherein the light irradiation unit includes a light source capable of emitting the pulsed light at a plurality of wavelengths that are mutually different, and
wherein the light source switches among the plurality of wavelengths in a period outside the period extending from a point at which the second time read out from the relation table elapses since the generation timing of the R-wave to a point at which the first time elapses.

11. A photoacoustic apparatus, comprising:
a control unit configured to set a light irradiation timing;
a light irradiation unit configured to irradiate a subject with pulsed light at the light irradiation timing;
an input unit configured to receive an instruction for driving the light irradiation unit from a user;
a reception unit configured to receive a photoacoustic wave generated in response to an irradiation of the subject by the pulsed light from the light irradiation unit and to output a signal;
an electrocardiogram acquisition unit configured to acquire an electrocardiogram signal of the subject; and
a subject information acquisition unit configured to acquire subject information on the basis of the signal,
wherein the control unit is configured to
set the light irradiation timing such that the subject is irradiated with the pulsed light at least once, on condition that the instruction has been received by the input unit, during a first time after a second time has elapsed since the generation timing of the R-wave, wherein the second time is extending from a generation timing of an R-wave in the electrocardiogram signal to an arrival timing at which a blood flow corresponding to the R-wave reaches the target region, and wherein the first time is extending from the generation timing of the R-wave in the electrocardiogram signal to a generation timing of a T-wave in the electrocardiogram signal,
set the light irradiation timing such that the subject is not irradiated with the pulsed light in a period outside a period extending from a point at which the second time elapses since the generation timing of the R-wave to a point at which the first time elapses.

12. The photoacoustic apparatus according to claim 11, wherein the light irradiation unit includes
an optical system configured to control an attenuation of the pulsed light from a light source, and
wherein the control unit sets the light irradiation timing by controlling the attenuation of the pulsed light in the optical system on the basis of the electrocardiogram signal.

13. A photoacoustic apparatus, comprising:
a control unit configured to set a light irradiation timing;
a light irradiation unit configured to irradiate a subject with pulsed light at the light irradiation timing;
a reception unit configured to receive a photoacoustic wave generated in response to an irradiation of the subject by the pulsed light from the light irradiation unit and to output a signal;
an electrocardiogram acquisition unit configured to acquire an electrocardiogram signal of the subject; and
a subject information acquisition unit configured to acquire subject information on the basis of the signal,
wherein the control unit is configured to
set the light irradiation timing such that the subject is irradiated with the pulsed light at least once during a first time after a second time has elapsed since the generation timing of the R-wave, wherein the second time is time extending from a generation timing of an R-wave in the electrocardiogram signal to an arrival timing at which a blood flow corresponding to the R-wave reaches the target region, and wherein the first time is time extending from the generation timing of the R-wave in the electrocardiogram signal to a generation timing of a T-wave in the electrocardiogram signal, set the light irradiation timing such that the subject is not irradiated with the pulsed light in a period outside a period extending from a point at which the second time elapses since the generation timing of the R-wave to a point at which the first time elapses.

14. The photoacoustic apparatus according to claim 13, wherein the light irradiation unit includes an optical system configured to control an attenuation of the pulsed light from a light source, and wherein the control unit sets the light irradiation timing by controlling the attenuation of the pulsed light in the optical system on the basis of the electrocardiogram signal.

15. The photoacoustic apparatus according to claim 14, wherein the light irradiation unit includes a light source capable of emitting the pulsed light at a plurality of wavelengths that are mutually different, and wherein the light source switches among the plurality of wavelengths in the period outside the period extending from the point at which the second time elapses since the generation timing of the R-wave to the point at which the first time elapses.

* * * * *